(12) United States Patent
Realff et al.

(10) Patent No.: US 9,631,057 B2
(45) Date of Patent: Apr. 25, 2017

(54) METHODS OF ENZYMATIC HYDROLYSIS

(75) Inventors: Matthew James Realff, Atlanta, GA (US); Ronald W. Smith, Ben Lomond, CA (US); Prabuddha Bansal, Atlanta, GA (US); Andreas Sebastian Bommarius, Atlanta, GA (US); Melanie Hall, Graz (AT); Jay Hyung Lee, Alpharetta, GA (US)

(73) Assignees: Texaco Inc., San Ramon; Georgia Tech Research Corporation, Atlanta ( * ) Notice: Subject to any disclaimer, the term of this patent is extended or adjusted under 35 U.S.C. 154(b) by 1430 days.

(21) Appl. No.: 12/942,906

(22) Filed: Nov. 9, 2010

(65) Prior Publication Data

US 2011/0244499 A1 Oct. 6, 2011

Related U.S. Application Data

(60) Provisional application No. 61/259,520, filed on Nov. 9, 2009.

(51) Int. Cl.

| C12P 19/24 | (2006.01) |
|---|---|
| C08H 8/00 | (2010.01) |
| C12P 19/02 | (2006.01) |
| C12P 19/14 | (2006.01) |
| C13K 1/02 | (2006.01) |
| G01N 21/3577 | (2014.01) |

(52) U.S. Cl.
CPC ................ *C08H 8/00* (2013.01); *C12P 19/02* (2013.01); *C12P 19/14* (2013.01); *C13K 1/02* (2013.01); *G01N 21/3577* (2013.01); *C12P 2203/00* (2013.01)

(58) Field of Classification Search
None
See application file for complete search history.

(56) References Cited

U.S. PATENT DOCUMENTS

| 5,865,898 A | 2/1999 | Holtzapple et al. |
| 8,236,536 B2 * | 8/2012 | Varanasi et al. ............. 435/165 |
| 2009/0011473 A1 | 1/2009 | Varanasi et al. |

OTHER PUBLICATIONS

Laureano-Perez et al., "Understanding Factors that Limit Enzymatic Hydrolysis of Biomass: Characterization of Pretreated Corn Stover", Applied Biochemistry and Biotechnology, 2005, vol. 121-124, pp. 1081-1099.

Chang et al., "Fundamental Factors Affecting Biomass Enzymatic Reactivity", Applied Biochemistry and Biotechnolgy, 2000, vol. 84-86, pp. 5-37.

PCT/US10/56072, filed Nov. 9, 2010, Notification of Transmittal of the International Search Report and the Written Opinion of the International Searching Authority dated Jan. 13, 2011, 12 pages.

* cited by examiner

*Primary Examiner* — Richard Hutson
(74) *Attorney, Agent, or Firm* — Howard V. Owens (57) ABSTRACT

In one embodiment the instant invention generally pertains to a method for producing glucose for fermentation. The method comprises first treating a biomass with acid and heat under conditions sufficient to produce a composition mixture comprising cellulose suitable for enzymatic hydrolysis. Next, at least a portion of the cellulose of step (a) is enzymatically hydrolyzed under conditions sufficient to form a composition comprising glucose. The glucose is then fermented. Advantageously, one or more reaction conditions are more efficient because they are selected by first measuring an initial hydrolysis rate of said biomass and then selecting one or more appropriate reaction conditions based upon said initial hydrolysis rate.

6 Claims, 7 Drawing Sheets

METHODS OF ENZYMATIC HYDROLYSIS

CROSS-REFERENCE TO RELATED APPLICATIONS

For purposes of United States patent practice, the contents of U.S. Provisional Application No. 61/259,520 is herein incorporated by reference in its entirety to the extent that it is not inconsistent.

FIELD OF THE INVENTION

The present invention pertains to improved methods for assessing value of a biomass in an enzymatic hydrolysis. The invention also pertains to improved methods of enzymatic hydrolysis which comprise using an initial hydrolysis rate to select or adjust one or more enzymatic reaction conditions.

BACKGROUND AND SUMMARY OF THE INVENTION

The enzymatic hydrolysis of cellulose to glucose has gained increased interest over the last ten years, and growing demand for economically sustainable biofuels points to an urgent need for reducing costs in their production. Cellulose, a polysaccharide made by many plants, is one of the most abundant organic compounds on Earth and therefore represents a potential goldmine for the biofuel industry. However, current enzymatic degradation of cellulose faces major issues that prevent its wide utilization to produce economically competitive biofuel.

Cellulose is hydrolyzed to glucose via the synergistic action of several enzymes. Endoglucanases (E.C. 3.2.1.4) break down cellulose chains at random positions within the cellulose chains whereas exoglucanases (i.e. cellobiohydrolases, E.C. 3.2.1.91) cleave off cellobiose specifically from the chain ends in a processive manner. Cellobiose is subsequently converted into glucose by β-glucosidase (E.C. 3.2.1.21). The exo-endo synergism is easily understood by the fact that endoglucanases provide more chain ends for cellobiohydrolases to act upon. The hydrolysis of insoluble, solid cellulose is a heterogeneous reaction, which cannot be described by kinetic models based just on Michaelis-Menten kinetics. After an initial phase of adsorption of cellulases on cellulose (fast comparatively to hydrolysis), the enzymes cleave off cellobiose and move along the same chain, hydrolyzing glycosidic bonds until an event that terminates cleavage occurs. As the reaction proceeds to intermediate degrees of conversion, the rate decreases dramatically, and the last part of the cellulose hydrolysis requires an inordinate amount of overall total reaction time. Several factors, both substrate- and enzyme-related, have been suggested to be responsible for this slowdown of rate, but so far no clear picture of what is limiting the reaction has been proposed. The substrate characteristics often implied in the slowdown of rate include surface area, porosity, degree of polymerization, crystallinity, and overall composition (complex substrates such as lignocellulosics vs. pure cellulose). For enzyme-related features, deactivation, inhibition, jamming, clogging, and imperfect processivity are often advanced as causes for slowdown.

One of the most controversial theories concerns the influence of crystallinity and the change of the degree of crystallinity during enzymatic hydrolysis. It is accepted that the initial degree of crystallinity of cellulose plays a major role as rate determinant in the hydrolysis reaction. A completely amorphous sample is hydrolyzed much faster than a partially crystalline cellulose, which has led to the currently widespread assumption that amorphous domains in a partially crystalline cellulose sample are hydrolyzed first, leaving crystalline parts to be hydrolyzed at the end, thus resulting in an increased crystallinity index and explaining the dramatic drop in rate at higher degrees of conversion.

However, studies of this phenomenon differ by the analytical methods (X-ray diffraction vs. solid state $^{13}$C-NMR), the nature of the substrate used (complex lignocellulosics vs. pure cellulose) and the source of the hydrolytic enzymes (mostly from *Trichoderma reesei* and other fungal strains). Several reviews have stated that it is still difficult to conclude that crystallinity is a key determinant of the rate of enzymatic hydrolysis. See, for example, (1) Lynd, L. R.; Weimer, P. J.; van Zyl, W. H.; Pretorius, I. S., Microbial cellulose utilization: Fundamentals and biotechnology. *Microbiology and Molecular Biology Reviews* 2002, 66, (3), 506-+; (2) Zhang, Y. H. P.; Lynd, L. R., Toward an aggregated understanding of enzymatic hydrolysis of cellulose: Noncomplexed cellulase systems. *Biotechnology and Bioengineering* 2004, 88, (7), 797-824; and (3) Mansfield, S. D.; Mooney, C.; Saddler, J. N., Substrate and enzyme characteristics that limit cellulose hydrolysis. *Biotechnology Progress* 1999, 15, (5), 804-816. Usually, different types of cellulose with different degrees of crystallinity were employed in these studies (such as cotton, cotton linter, Avicel, filter paper, or bacterial cellulose). Their cellulase-catalyzed degradation gave hydrolysis rates directly related to the initial crystallinity index of the cellulose sample. To correctly relate crystallinity index with hydrolysis rate, it is of prime importance to study samples that have the same basic composition and provenance. More importantly, pure cellulose is superior to complex substrates, as the presence of lignin or hemicellulose may interfere with the cellulase action and reduce accessibility (and therefore hydrolysis rates).

Another important criteria related to hydrolysis rate involves adsorption capacity of cellulases onto cellulose. The rate of hydrolysis has been shown to be proportional to the amount of adsorbed enzymes. Additionally the amount of adsorbed endoglucanases was found to be strictly related to the hydrolyzability of crystalline cellulose. Furthermore, the degree of crystallinity of cellulose influences adsorption at a given protein loading and maximum adsorption constant has been shown to be greatly enhanced with low crystallinity indexes. The same work concluded that the effective binding was the limiting parameter in hydrolysis rate in the case of cellulose with low degrees of crystallinity (despite high adsorption constant).

Amorphous cellulose is a favored modification to investigate cellulase activity. Obtained after treatment with 85% phosphoric acid, the cellulose obtained in this way, PASC (phosphoric acid swollen cellulose), results from complete dissolution of the sample and the treatment was shown to have no impact on the reducing-end concentration of the cellulose sample (i.e. its degree of polymerization). The effect of various phosphoric acid concentrations has only been investigated across a narrow range of acid concentrations or mainly at low concentrations. Recently, Zhang et al. showed that the concentration of phosphoric acid used to generate swollen cellulose dictates the rate of enzymatic hydrolysis by controlling the state of cellulose solubilization (*Biomacromolecules* 2006, 7, (2), 644-648).

Accordingly, there remains a need for determining the main causes of rate limitations in the enzymatic hydrolysis of, for example, Avicel and other biomass materials, and especially the role of, for example, crystallinity and adsorption on cellulose susceptibility to enzymatic degradation. Both $^{13}$C-NMR solid-state spectroscopy and X-ray crystallography may be applied to investigate the crystallinity of pure cellulose (Avicel) at different degrees of conversion by cellulases from *Trichoderma reesei*, the most commonly studied cellulase-producing organism. Cellulose (Avicel) with controlled degrees of crystallinity may be generated with phosphoric acid solutions of precisely calibrated concentration. These cellulose samples from the same source may be employed to investigate and elucidate the relationship between degree of crystallinity, adsorption and enzymatic hydrolysis rates.

In general terms the instant invention pertains in one embodiment to a method for assessing value of a biomass in an enzymatic hydrolysis comprising first measuring an initial hydrolysis rate of the biomass and then correlating the measured initial hydrolysis rate with an established crystallinity index of standard cellulosic material to project a crystallinity indicative of overall enzymatic hydrolysis susceptibility.

In another embodiment the instant invention generally pertains to a method for producing glucose for fermentation. The method comprises:

(a) treating a biomass with acid and heat under conditions sufficient to produce a composition mixture comprising cellulose suitable for enzymatic hydrolysis;

(b) enzymatically hydrolyzing at least a portion of the cellulose of step (a) under conditions sufficient to form a composition comprising glucose; and (c) fermenting glucose by, for example, utilizing glucose in an aerobic or anaerobic fermentation process. Typically, one or more reaction conditions of steps (a), (b), or (c) are selected by first measuring an initial hydrolysis rate of said biomass and then selecting one or more appropriate reaction conditions based upon said initial hydrolysis rate.

In yet another embodiment, the invention pertains to a method of using the initial hydrolysis rate to improve the efficiency of an enzymatic hydrolysis. The method comprises:

(a) measuring the initial hydrolysis rate of a biomass to be subjected to hydrolysis and correlating the measured initial hydrolysis rate with an established crystallinity index of standard cellulosic material to project a crystallinity indicative of overall enzymatic hydrolysis susceptibility;

(b) selecting a hydrolysis enzyme and determining the required amount of said enzyme to produce cellulosic sugars with said biomass;

(c) determining the overall hydrolysis rate at said required amount of said enzyme;

(d) selecting or adjusting one or more of the following enzymatic reaction conditions: pre-treatment step, reaction time, reaction temperature, type of enzyme, and amount of enzyme; and (e) enzymatically hydrolyzing a biomass using one or more of said selected conditions.

BRIEF DESCRIPTION OF THE FIGURES

FIGS. 1(*a*), 1(*b*), and 1(*c*) illustrate effects of phosphoric acid concentration.

FIGS. 7 (*a*), 7(*b*), and 7(*c*) illustrate adsorption, crystallinity index, and initial rates at two cellulase loadings.

DETAILED DESCRIPTION OF THE INVENTION

In general terms the instant invention pertains in one embodiment to a method for assessing value of a biomass in an enzymatic hydrolysis. The method comprises first measuring an initial hydrolysis rate of the biomass that is contemplated for enzymatic hydrolysis. The biomass may be any that is contemplated for enzymatic hydrolysis. That is, the origin and type of the biomass employed is not particularly critical so long as it is capable of undergoing the steps of the instant processes. In one embodiment a particularly preferable feedstock is a lignocellulosic feedstock material such as a plant biomass typically comprised of, for example, cellulose, hemicellulose, poly(aromatics), such as lignin, extractives, ash, and mixtures thereof. Such lignocellulosic materials may often comprise carbohydrate polymers (cellulose and hemicelluloses) which may bond to the lignin. Biomass comes in many different types, which may be grouped into a few main categories: wood or forestry residues, including sawmill and paper mill discards, municipal paper waste, algae, agricultural residues, including corn stover (stalks and straw), and sugarcane bagasse, and dedicated energy crops, which are mostly composed of fast growing tall, woody grasses such as, for example, switchgrass. Any of the aforementioned and others may find use in the instant invention.

The initial hydrolysis rate may be measured by any convenient method so long as it is substantially reliable and/or substantially reproducible. Such methods include, for example, x-ray diffraction, solid state cross-polarization/magic angle spinning nuclear magnetic resonance, infrared spectroscopy, differential scanning calorimetry, or a combination thereof. The use of infrared spectroscopy is described at, for example, Mary L. Nelson & Robert T. O'Connor, Relation of certain infrared bands to cellulose crystallinity and crystal lattice type. Part II. A new infrared ratio for estimation of crystallinity in celluloses I and II, Journal of Applied Polymer Science, 2003, 8, 1325-1341). The use of differential scanning calorimetry (DSC) is described at, for example, Maria Silvia Bertran & Bruce E. Dale, Determination of cellulose accessibility by differential scanning calorimetry, Journal of Applied Polymer Science, 1986, 32, 4241-4253. In one embodiment, the method described in the examples below is employed.

Next, the measured initial hydrolysis rate may be correlated with an established crystallinity index of a standard cellulosic material to project a crystallinity indicative of overall enzymatic hydrolysis susceptibility. The established crystallinity index may be determined by, for example, applying multivariate statistical analysis to X-ray diffraction spectra, solid state cross-polarization/magic angle spinning nuclear magnetic resonance spectra, infrared spectra, differential scanning calorimetry heat capacity temperature plots, or a combination thereof. In one embodiment, multivariate statistical analysis is applied to X-ray diffraction spectra as described in the examples below.

That is, in one specific embodiment to calculate crystallinity indices, normalized X-ray diffraction spectra may be expressed as a linear combination of normalized untreated cellulose (e.g., Avicel or FC) and amorphous cellulose spectra. Principal component analysis (PCA) may then be applied to the spectroscopic data (e.g., separately to Avicel and FC spectra sets) and the principal component scores can then be related to calculated crystallinities. This often reveals the dimensionality of the X-ray spectra data. Cellulose mixtures with varying fractions of untreated and amorphous Avicel as an example may be prepared to validate the predicted crystallinity values. Since initial hydrolysis rates may follow a linear trend with the calculated crystallinity index, principal component regression can likely be used to successfully predict the initial hydrolysis rates from X-ray spectra.

The standard cellulosic material for the established crystallinity index may be selected from any convenient material. In one embodiment a standard cellulosic material is selected from the group consisting of Avicel, fibrous cellulose, bacterial cellulose, cotton, lignocellulosic material, and mixtures thereof. Particularly preferable lignocellulosic materials may include, for example, switchgrass, loblolly pine, bagasse, corn stover, poplar tree, miscanthus, mixtures thereof, etc.

If desired, one may employ further steps which use the measured initial hydrolysis rate. Such steps may include one, two, or more of the following: (a) using the initial hydrolysis rate to determine an amount of hydrolysis enzyme required to produce cellulosic sugars; (b) using the initial hydrolysis rate to determine the overall hydrolysis rate with a particular quantity of hydrolysis enzymes; and (c) using the initial hydrolysis rate to select one or more reaction conditions selected from the group consisting of pre-treatment, reaction time, reaction temperature, type of enzyme, and amount of enzyme. In this manner, one may enzymatically hydrolyze a biomass of virtually any type in a more efficient manner using one or more the selected or adjusted conditions.

In another embodiment, the instant invention pertains to a method for producing glucose. The glucose may be fermented by, for example, utilizing glucose in an aerobic or anaerobic fermentation process. The method comprises first (a) treating a biomass with acid and heat under conditions sufficient to produce a composition mixture comprising cellulose suitable for enzymatic hydrolysis. The biomass may be selected from, for example, any of those described above. The type of acid, amount of heat and other treatment conditions are not particularly critical so long as the result is a composition mixture comprising cellulose suitable for enzymatic hydrolysis. A number of such suitable conditions are described in the literature references and in the examples below.

Next, in step (b) at least a portion of the cellulose of step (a) is enzymatically hydrolyzed under conditions sufficient to form a composition comprising glucose. The conditions of enzymatic hydrolysis are not particularly critical so long as a composition comprising glucose results and a wide variety of suitable conditions are described in the literature references and in the examples below. The glucose may then be utilized in an aerobic or anaerobic fermentation process using suitable conditions to form a desired fermentation product or products. Such a product or products may be selected from the group consisting of alcohols, fatty alcohols, hydrocabons, fatty acids, tryglycerides, terpenes, and combinations thereof.

As described above, there are a wide variety of conditions available for steps (a), (b), and (c) of the previously described method. One of the advantages of the present method is that the conditions may be selected or determined in order to make any one or more of steps (a), (b), or (c) more efficient. That is, one or more reaction conditions of steps (a), (b), or (c) may be selected or determined by first measuring an initial hydrolysis rate of a biomass and then selecting one or more appropriate reaction conditions based upon said initial hydrolysis rate. In one embodiment, one or more appropriate conditions may be determined by correlating the measured initial hydrolysis rate with an established crystallinity index of standard cellulosic material to project a crystallinity indicative of overall enzymatic hydrolysis susceptibility. These one or more appropriate conditions may be selected from, for example, the group consisting of type of enzyme, amount of enzyme, reaction time, and reaction temperature.

As described above and in the examples below, an initial hydrolysis rate may be measured by, for example, x-ray diffraction, solid state cross-polarization/magic angle spinning nuclear magnetic resonance, infrared spectroscopy, differential scanning calorimetry, or a combination thereof. And similarly the established crystallinity index may be determined by, for example, applying multivariate statistical analysis to X-ray diffraction spectra, solid state cross-polarization/magic angle spinning nuclear magnetic resonance spectra, infrared spectra, differential scanning calorimetry heat capacity temperature plots, or a combination thereof.

In another embodiment, the invention pertains to a method of using the initial hydrolysis rate to improve the efficiency of an enzymatic hydrolysis. The method comprises first measuring the initial hydrolysis rate of a biomass to be subjected to hydrolysis and correlating the measured initial hydrolysis rate with an established crystallinity index of standard cellulosic material to project a crystallinity indicative of overall enzymatic hydrolysis susceptibility. The selection of biomass, as well as, the measurement and correlation of the hydrolysis rate are as described above.

Next, the hydrolysis enzyme and amount useful to produce cellulosic sugars with the biomass is determined along with the overall hydrolysis rate for the amount of enzyme. Enzymatic reaction conditions may then be selected or adjusted based upon, for example, a measured initial hydrolysis rate and/or correlation with crystallinity index. Such condition include, for example, pre-treatment step, reaction time, reaction temperature, type and amount of enzyme, etc. The biomass may then be enzymatically hydrolyzed using one or more of said selected or adjusted conditions. In many cases, the hydrolysis may be more efficient or optimal using the aforementioned methods.

In another embodiment, the instant invention may be beneficial in, for example, selecting a biomass having a suitable crystallinity for a contemplated hydrolysis for further study or implementation. In this manner, one may efficiently assess the value of a given material for enzymatic hydrolysis in a small amount of time. In alternative embodiments, the method may be accomplished in less than 1 day, or less than 12 hours, or less than 1 hour, or less than 10 minutes, or less than 5 minutes, or in some cases in less than 2 minutes. In some embodiments such a method may be accomplished without resort to extensive x-ray crystallography, solid-state NMR, or enzymatic hydrolysis which methods may take much longer and/or be more expensive and/or require more specialized equipment. The instant method may be a quick and useful predictor of a given biomass's ease of hydrolyzability, overall reaction time, and/or overall amount enzyme that may be required. This advantageously allows the practitioner to quickly screen many potential biomass sources to find ones that may be more useful for hydrolysis by exhibiting, for example, a suitable crystallinity.

In another embodiment the instant invention generally pertains to a method for improved enzymatic hydrolysis of biomass. This method comprises first measuring an initial hydrolysis rate of a biomass and then using the initial hydrolysis rate to select or adjust one or more of the following enzymatic reaction conditions: type of biomass, pre-treatment step (if employed), reaction time, reaction temperature, type of enzyme, and amount of enzyme. Next, a biomass is enzymatically hydrolyzed using one or more of said selected or adjusted conditions. In some embodiments, the method may be accomplished without resort to extensive x-ray crystallography, solid-state NMR, or enzymatic hydrolysis which methods may take much longer and/or be more expensive and/or require more specialized equipment.

LEGENDS FOR FIGURES IN EXAMPLES

Figure 1A:
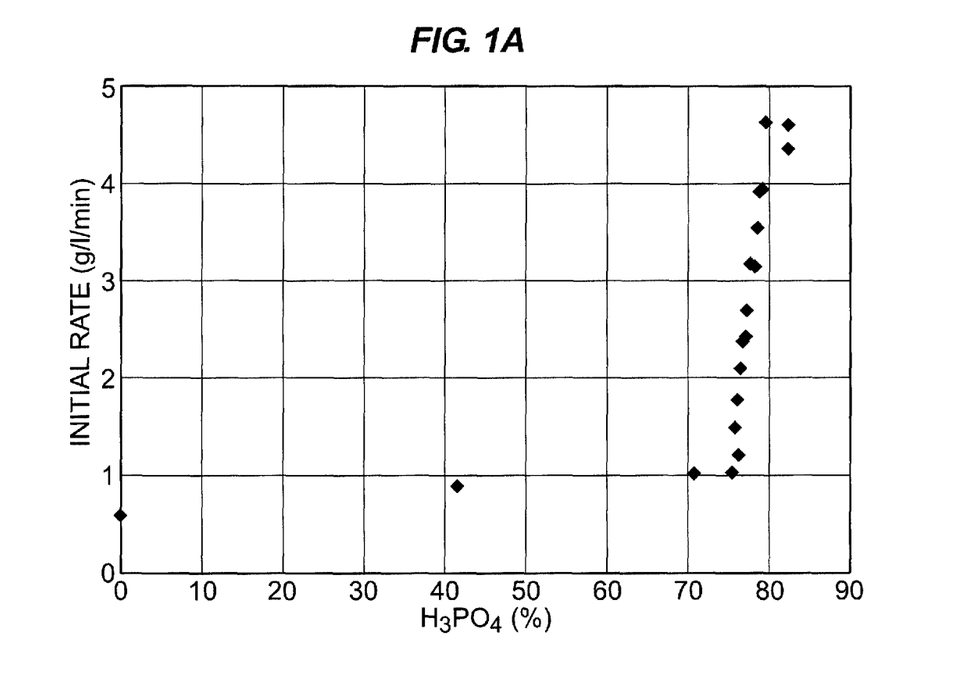
Figure 1B:
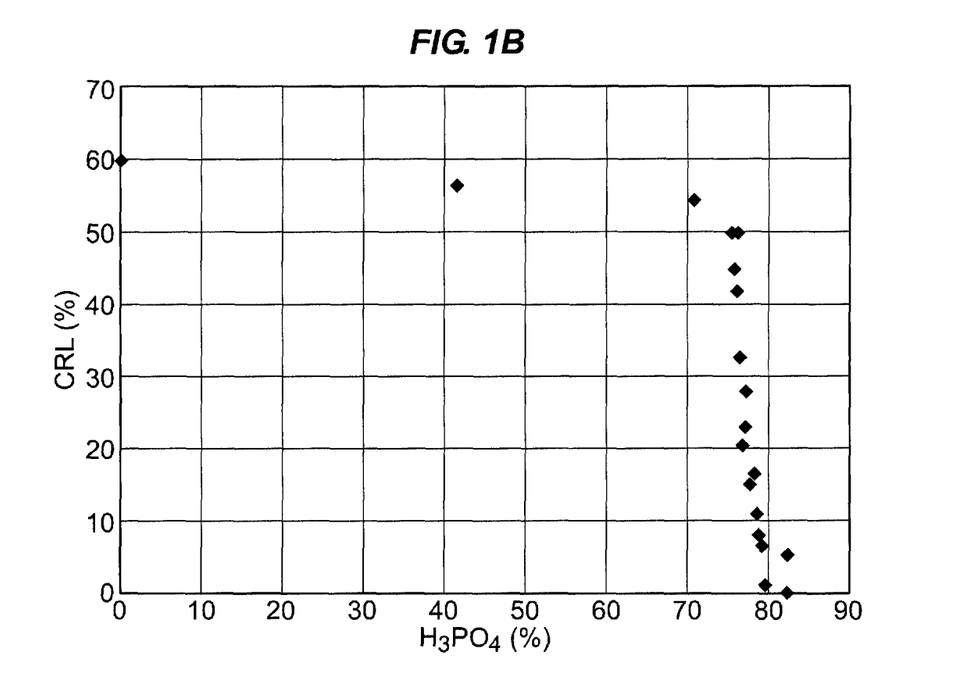
Figure 1C:
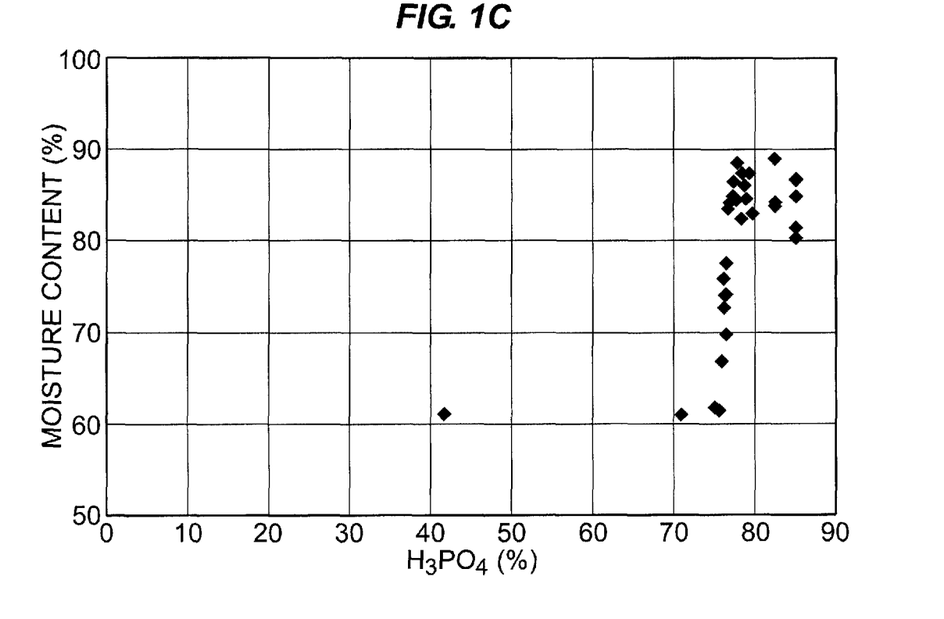

FIG. 1. a. Effect of phosphoric acid concentration on: a. initial rate of Avicel enzymatic hydrolysis (glucose produced in the first 2 min of the reaction with cellulases); b. crystallinity index CrI obtained from X-ray diffraction data; c. moisture content of cellulose samples after treatment with phosphoric acid (measurement performed after tightly controlled filtration and subsequent drying at 60° C.).

Figure 2:
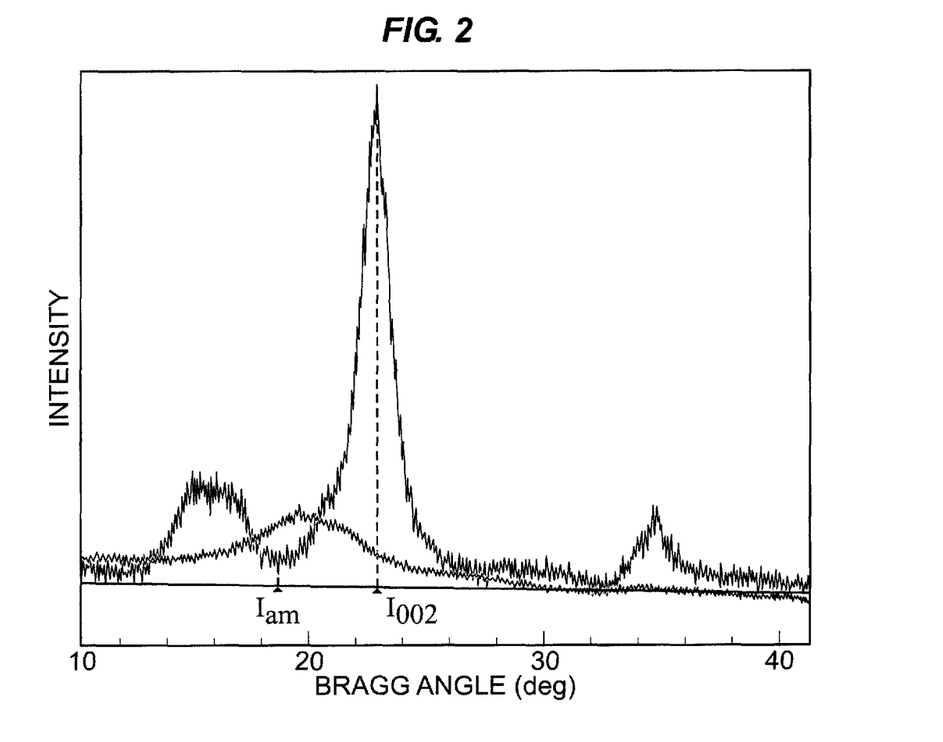
FIG. 2 illustrates X-Ray diffraction pattern of two Avicel having differing amounts of crystallinity.

FIG. 2. X-Ray diffraction pattern of microcrystalline cellulose Avicel (red) and amorphous Avicel (blue) generated with 85% phosphoric acid (reflection around 20° is attributed to amorphous parts and gives CrI=0% based on peak intensity method[71]). X-axis: Bragg angle (2θ). $I_{002}$ represents the maximum intensity at 2θ=22.5°, $I_{am}$ shows the minimum intensity at 2θ=18° used to calculate crystallinity in the peak height method, and the straight line represents the background (see corresponding experimental section).

Figure 3:
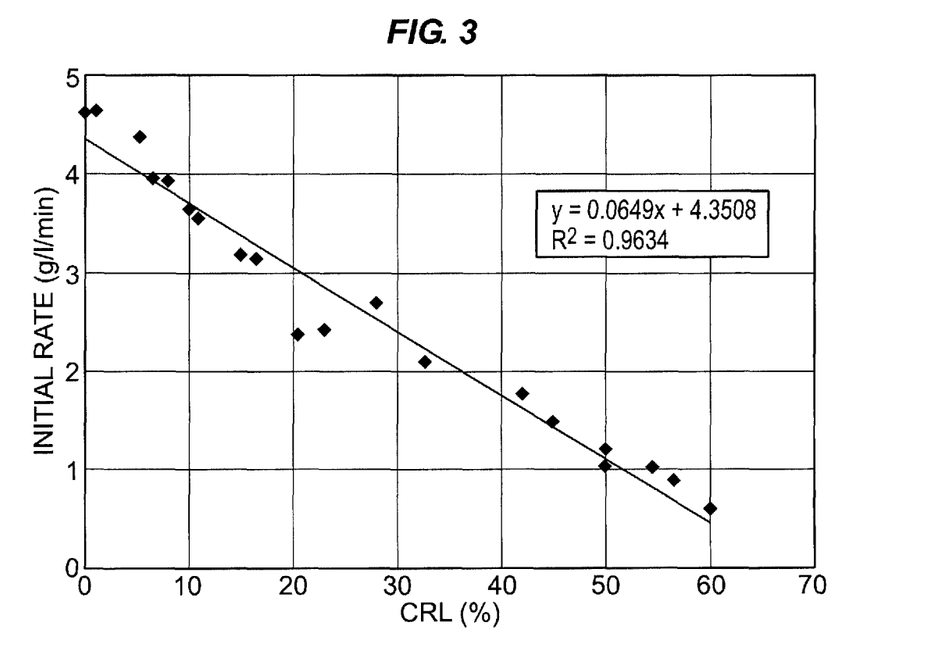
FIG. 3 illustrates effect of crystallinity on initial rate.

FIG. 3. Effect of crystallinity on the initial rate in Avicel enzymatic hydrolysis (glucose produced in the first 2 min of the reaction with cellulases).

Figure 4:
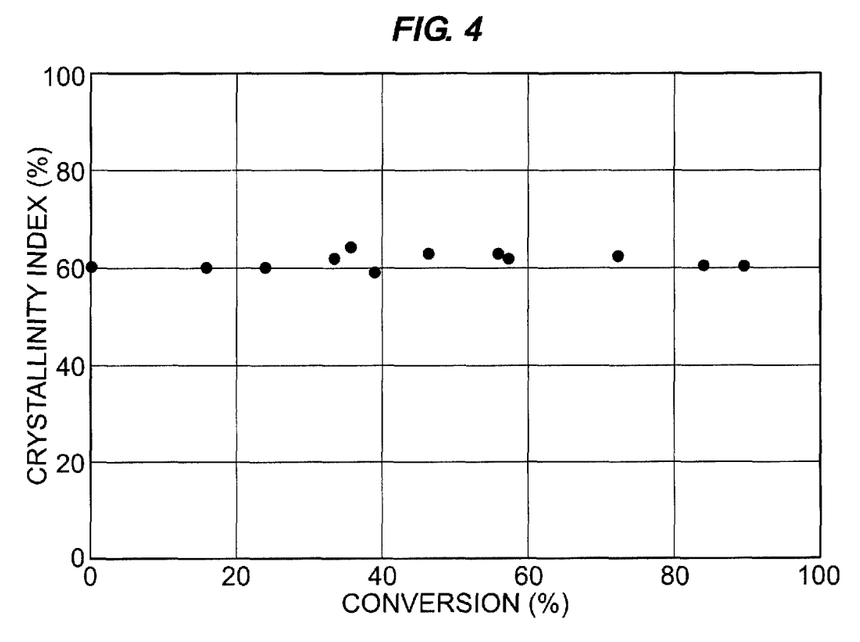
FIG. 4 illustrates crystallinity index of Avicel monitored during hydrolysis.

FIG. 4. Crystallinity index of Avicel monitored during hydrolysis with cellulases via CP/MAS $^{13}$C-NMR.

Figure 5:
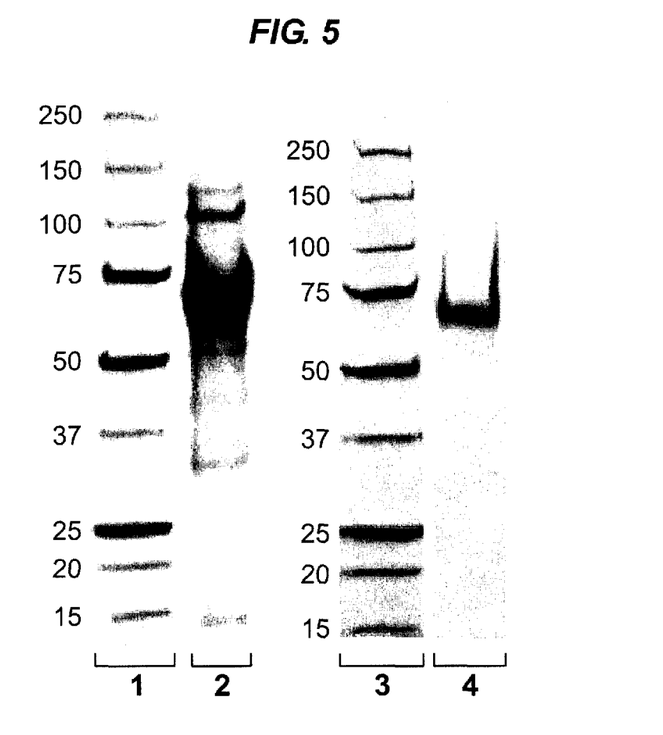
FIG. 5 illustrates SDS-PAGE of extracellular proteins.

FIG. 5. SDS-PAGE of extracellular proteins produced by *Trichoderma reesei*, and purified Cel7A. Lanes 1 and 3: ladder, lane 2: proteins in the liquid medium containing overexpressed Cel7A (after cells were filtered off) and lane 4: Cel7A purified by anion-exchange chromatography (67 kDa)

Figure 6:
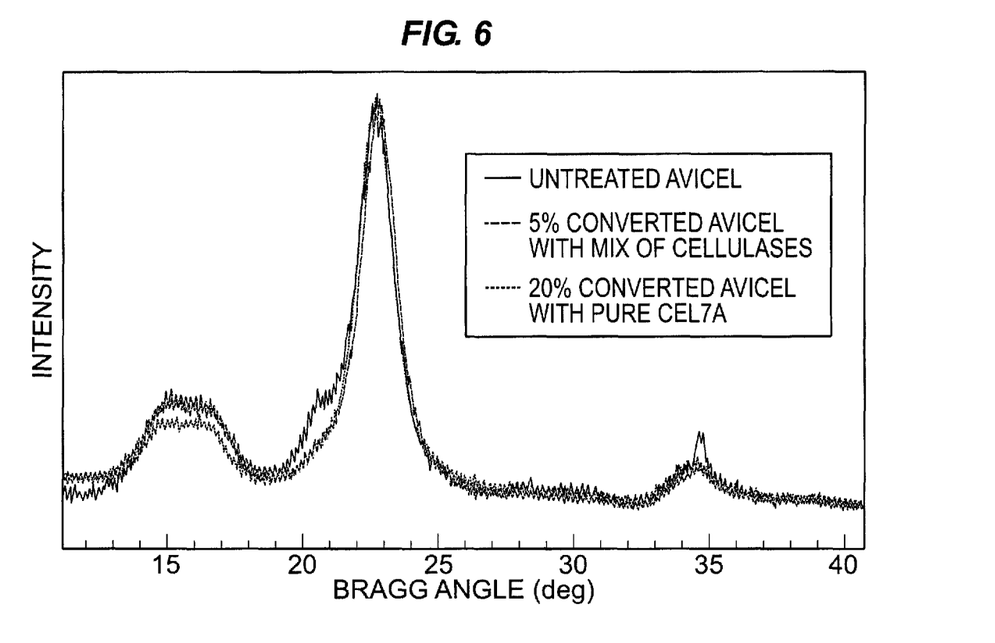
FIG. 6 illustrates X-Ray diffraction pattern of untreated Avicel and partially converted cellulose.

FIG. 6. X-ray diffraction patterns of untreated Avicel and partially converted cellulose between 10 and 40° (2θ). X-axis: Bragg angle (2θ). The reflection of face (021) of the crystal (centered around 21°) is visible only for untreated Avicel.

Figure 7A:
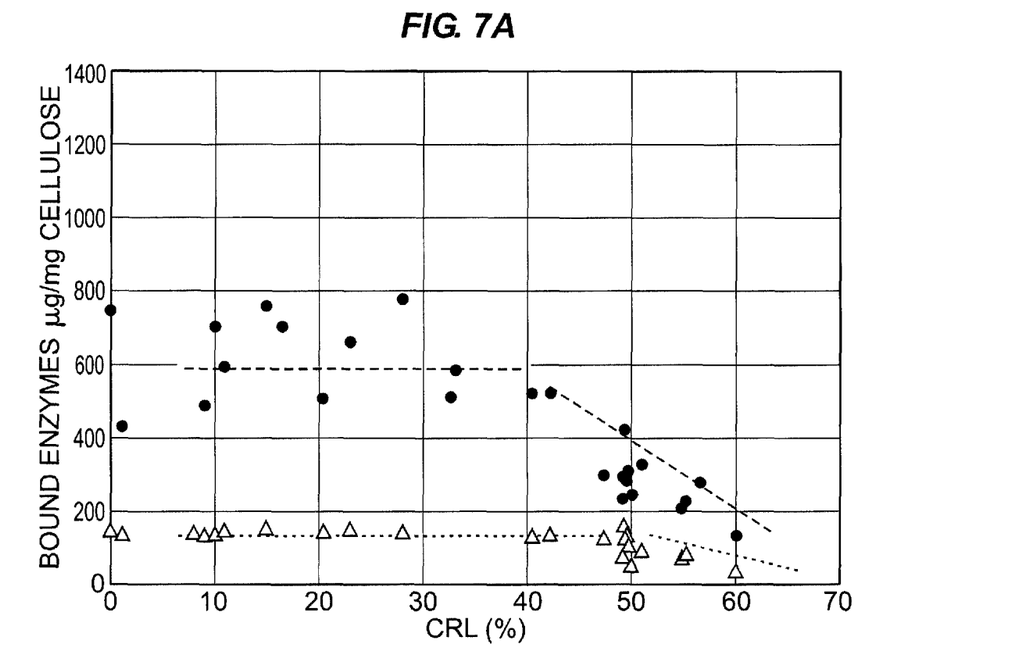
Figure 7B:
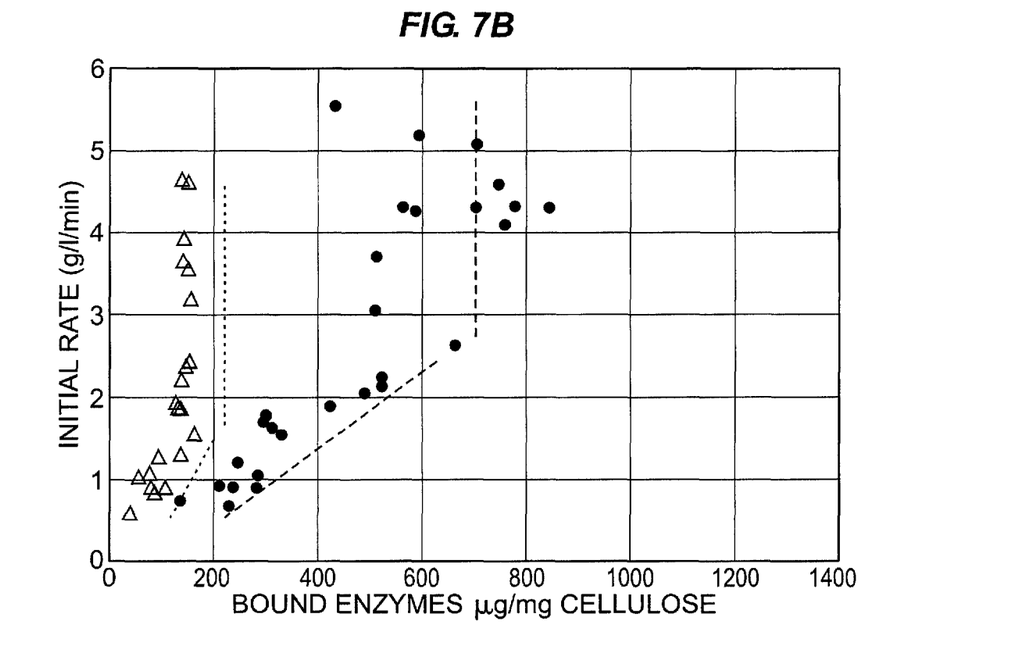
Figure 7C:
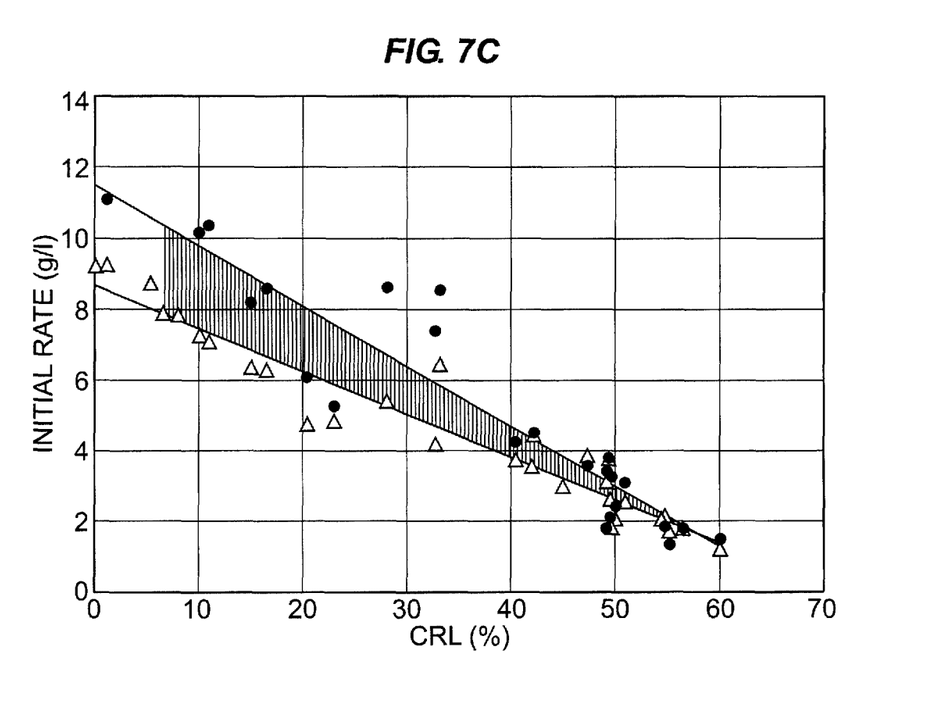

FIG. 7. Adsorption, crystallinity index and initial rates at two cellulases loading: Δ175 μg/mg cellulose; •1230 μg/mg cellulose. Initial rates correspond to the amount of glucose produced over a 2 min reaction (20 mg cellulose/ml, corresponding amount of cellulases and excess of β-glucosidase, 50° C.). Adsorption studies were conducted at 4° C. over 30 min incubation time. a. adsorption vs crystallinity index; b. initial rate vs adsorption; c. initial rate vs crystallinity index, where grey shaded area represents the importance and role of adsorption on enzymatic rate.

Figure 8A:
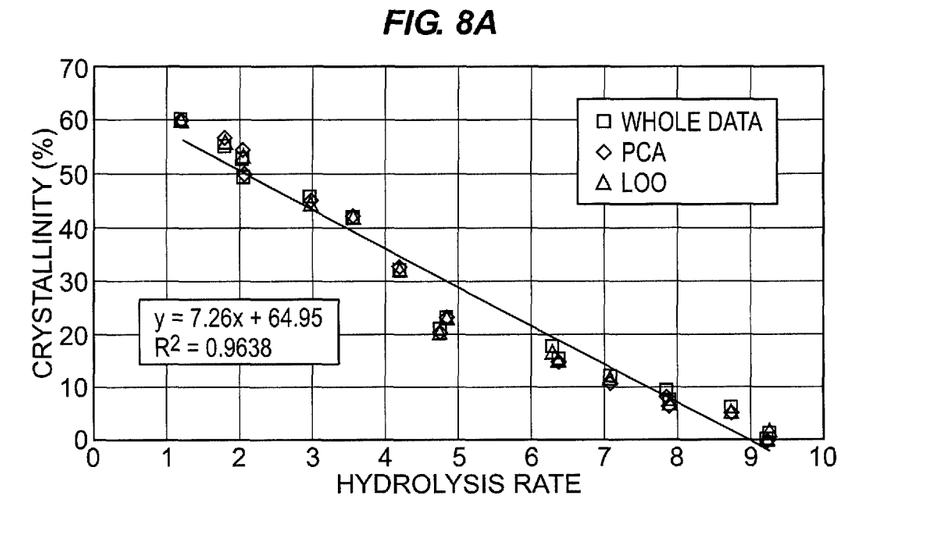
FIG. 8*a* shows the calculated crystallinity vs. enzymatic hydrolysis rate for Avicel.
Figure 8B:
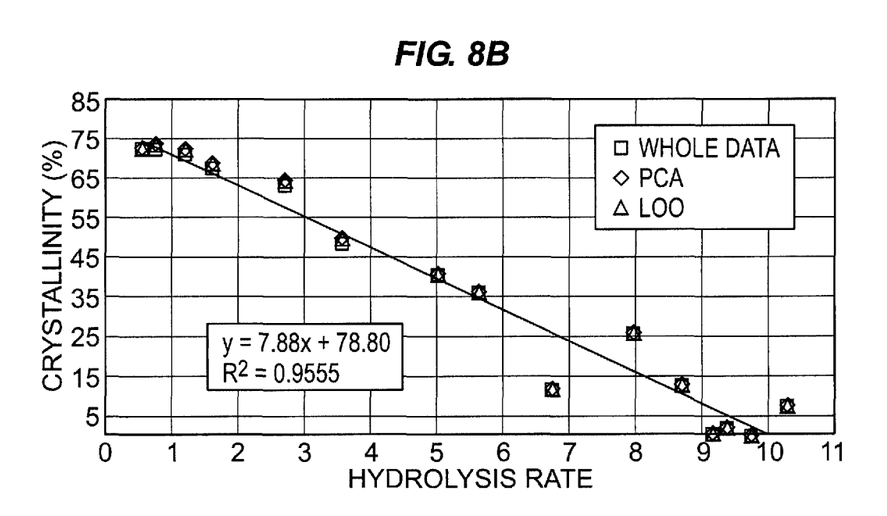
FIG. 8*b* shows the calculated crystallinity vs. enzymatic hydrolysis rate for fibrous cellulose.

FIG. 8. Calculated crystallinity vs. enzymatic hydrolysis rate. The hydrolysis rates correspond to the amount of glucose produced in the first 2 min of the reaction with cellulases. The linear equations shown are the fits between degrees of crystallinity calculated with whole spectra and hydrolysis rates.

Example 1

Avicel

Material and Chemicals

All chemicals and reagents were purchased from Sigma unless otherwise stated. Avicel PH-101, cellulases from *Trichoderma reesei* (159 FPU/ml) and β-glucosidase (from almonds, 5.2 U/mg) were from Sigma, phosphoric acid (85%) was from EMD. *Trichoderma reesei* QM9414 strain was obtained from ATCC (#26921). BCA protein assay kit was obtained from Thermo Fischer Scientific.

Phosphoric Acid Pretreatment 1 g of slightly moistened Avicel was added to 30 ml of an ice-cold aqueous phosphoric acid solution (concentration ranging from 42% up to 85% wt) and allowed to react over 40 min with occasional stirring. After addition of 20 ml of ice-cold acetone and subsequent stirring, the resulting slurry was filtered over a fritted filtered-funnel and washed three times with 20 ml ice-cold acetone, and 4 times with 100 ml water. The resulting cellulose was used as such in enzymatic hydrolysis experiments, after moisture content was estimated upon oven-drying at 60° C. overnight. Samples were freeze-dried prior to X-ray diffraction measurements.

Enzymatic Hydrolysis of Cellulose

A suspension of Avicel (20 g/l) in sodium acetate buffer (1 ml, 50 mM, pH 5) was hydrated during 1 h under stirring at 50° C. β-Glucosidase (15 kU/l) and cellulases (24 ml/l, 3.4 g/l total protein) were added and the mixture was stirred at 50° C. At desired time points, samples were centrifuged, and glucose content in the supernatant was measured via the dinitrosalicylic acid (DNS) assay. For crystallinity measurements at various conversion levels, reactions were run on a 15 ml scale and after centrifugation and washing with buffer and water, recovered cellulose was either freeze-dried, oven-dried (60° C.) or air-dried. When Cel7A was used as single cellulase component, 92 μg of purified enzyme per mg of Avicel were added to the reaction mixture.

Determination of Glucose Content

Glucose released from cellulose was measured using the DNS assay, as published before[28]. The calibration curve was generated with pure glucose standards. DNS assay was compared to HPLC analysis and was found to yield identical conversion results.

Determination of the Degree of Crystallinity of Cellulose
X-Ray Diffraction

X-ray diffraction patterns of cellulose samples obtained after freeze-drying were recorded with an X'Pert PRO X-ray diffractometer at room temperature from 10-60°, using Cu/Kα$_1$ irradiation (1.54 Å) at 45 kV and 40 mA. Scan speed was 0.021425°/sec with a step size of 0.0167°. CrI was calculated using peak intensity method[71]:

$$CrI = \frac{I_{002} - I_{am}}{I_{002}} \times 100$$

where $I_{002}$ is the intensity of the peak at 2θ=22.5°, and $I_{am}$ is the minimum in intensity corresponding to amorphous content at 2θ=18°. Freeze-drying showed no impact on the crystallinity of untreated Avicel.

Solid State $^{13}$C-NMR

The solid-state cross polarization/magic angle spinning (CP/MAS) $^{13}$C-NMR experiments were performed on a Bruker Avance/DSX-400 spectrometer operating at frequencies of 100.55 MHz for $^{13}$C. All the experiments were carried out at ambient temperature using a Bruker 4-mm MAS probe. The samples (~35% moisture content) were packed in 4 mm zirconium dioxide rotors and spun at 10 kHz. Acquisition was carried out with a CP pulse sequence using 5 μs pulse and 2.0 ms contact pulse. CrI was calculated according to literature[28]

$$CrI = \frac{A_{86-92\,ppm}}{A_{79-86\,ppm} - A_{86-92\,ppm}} \times 100$$

where $A_{86-92\,ppm}$ and $A_{79-86\,ppm}$ are the areas of the crystalline, resp. amorphous C4 carbons signal of cellulose.

Oven-drying (60° C.) showed no impact on the crystallinity of untreated Avicel.

Multivariate Statistical Analysis of X-Ray Data

The crystallinity index of cellulose samples was calculated by quantifying the contribution of amorphous cellulose (PASC) and Avicel to its (normalized) X-ray diffraction spectra. A full discussion may be found in Bansal, P.; Hall, M.; Realff, M. J.; Lee, J. H.; Bommarius, A. B., Multivariate statistical analysis of X-ray data from cellulose: A new method to determine degree of crystallinity and predict hydrolysis rates. 101 Bioresource Technol. 4461-4471 (2010) and/or Hall et al., "Cellulose Crystallinity—a key predictor of the enzymatic hydrolysis rate", FEBS Journal 277 (2010) 1571-1582, each of which is incorporated by reference herein for purposes of U.S. patent practice.

$$I_j(2\theta) = f_j I_P(2\theta) + (1-f_j) I_C(2\theta) + \epsilon$$

Where $I_j$ (2θ) is the intensity of the $j^{th}$ sample at diffraction angle 2θ, $I_p$ (2θ) is the intensity of PASC at diffraction angle 2θ, $I_C$ (2θ) is the intensity of untreated Avicel at diffraction angle 2θ, $f_j$ is the contribution of PASC to the spectrum, ϵ is the random error.

$\hat{f}_j$, the least square estimate of $f_j$, was used to estimate the crystallinity by multiplying the contribution of Avicel $(1-\hat{f}_j)$ by its crystallinity (calculated by CP/MAS $^{13}$C-NMR to be 60%):

$$Cri_j = (1-\hat{f}_j) * Cri_C$$

where $Cri_j$ is the crystallinity (in percentage) of the $j^{th}$ sample of Avicel, $Cri_C$ is the crystallinity of Avicel (60%).

Crystallinity was also calculated after principal component analysis (PCA) of the X-ray data set of all the samples. It was found that only one principal component was sufficient to capture the variation in the data sets. The reconstructed spectra (from one principal component) were then used in the equations above to calculate the crystallinity, and the values were found to be very close to the ones calculated by using the whole spectra.

Cel7A Purification

*Trichoderma reesei* QM9414 was grown on potato dextrose agar plate under light illumination. Spores were harvested and used to inoculate the liquid medium (minimal medium: $(NH_4)_2SO_4$ 5 g/l, $CaCl_2$ 0.6 g/l, $MgSO_4$ 0.6 g/l, $KH_2PO_4$ 15 g/l, $MnSO_4.H_2O$ 1.5 mg/l, $FeSO_4.7H_2O$ 5 mg/l, $CoCl_2$ 2 mg/l, $ZnSO_4$ 1.5 mg/l) supplemented with glucose (2%). After 3 days at 28° C. and 150 rpm, the fungus was grown on lactose (2%) in minimal medium for up to 12 days at 28° C. and 150 rpm. After filtration over glass-microfiber filter (GF/A 1.6 μm), the filtrate was diafiltered by repeated concentration and dilution with sodium acetate buffer (50 mM, pH 5.5) using a polyethersulfone membrane (MWCO 10 kDa). The concentrate was purified by means of anion-exchange chromatography using a Q-Sepharose Fast Flow with a 10 mM to 500 mM sodium acetate gradient (pH 5.5). Cel7A was eluted in the last peak, and purity was confirmed by SDS-PAGE. Enzyme concentrations were estimated by the Bradford assay, using bovine serum albumin as standard.

Adsorption Study

Cellulose samples (20 mg/ml) in NaOAc buffer (50 mM, pH 5) were incubated at 50° C. for 1 h under agitation (900 rpm), then cooled down to 4° C. Cellulases were added in various amounts and the mixture was further agitated for 30 min. After centrifugation, the supernatant was collected and protein content analysis was performed using the BCA protein assay (as described in Pierce® BCA Protein Assay Kit.

Results and Discussion

Cellulose Crystallinity and Cellulase Hydrolysis Rate

Various types of (ligno)cellulosic substrate are employed in current enzymatic hydrolysis studies and thus are a source of discrepancies in results and potential confusion to the challenging problem of understanding cellulase mode of action[31]. The presence of hemicellulose, and especially lignin, a strong adsorbent on cellulose, in lignocellulosics often interferes with the enzymatic activity of cellulases on cellulose[14, 29, 38]. To avoid such interference, we used Avicel, a commonly used, commercially and reproducibly obtainable pure cellulose substrate with well-characterized structure and an average degree of crystallinity of 60% (measured via solid state $^{13}$C-NMR).

Phosphoric Acid Pretreatment

First, to validate the efficiency of the phosphoric acid pretreatment, acid pretreated samples were hydrolyzed with cellulases (and an excess of β-glucosidase to remove product inhibition and fully convert cellobiose to glucose) and initial hydrolysis rate was calculated as production of glucose after 2 min reaction time. As expected, the more concentrated the phosphoric acid solution, the higher the sugar production (FIG. 1a), so that the pretreatment procedure was regarded as efficient. Samples treated with pure phosphoric acid solution (max. 85%) gave amorphous cellulose as proven by X-ray diffraction analysis[74] (FIG. 2, blue diffraction pattern). Besides, a high amount of glucose (4.75 g/l/min) was produced from the cellulose sample pretreated with the most concentrated acid solution (85%), and all Avicel was converted in less than 2.5 h, compared to over 96 h necessary for untreated Avicel (data not shown).

Phosphoric acid pretreatment has been used to create cellulose samples of various surface areas and this parameter was found to be related to enzymatic rate[49]. A recent study using phosphoric acid to increase cellulose accessibility in lignocellulosics suggested the presence of a critical point in phosphoric acid concentration below which enzymatic hydrolysis was slow, and above which cellulose was easily dissolved[56]. Our own results (FIGS. 1a-c) confirm that there is a steep change in reactivity (i.e. glucose production) from 1 to 4.75 g/l/min (FIG. 1a), not as a step change, but a steep continuum in a narrow range of phosphoric acid content between 75 and 80%. No further increase was observed beyond 80% (with a maximum phosphoric acid concentration possible of 85%, as commercially available), close to the 81% obtained by Moxley et al. for maximum glucan digestibility[56]. Below 75%, the glucose production rate tends to level off to reach a minimum obtained with untreated Avicel (0.6 g/l/min glucose at 0% phosphoric acid). Thus, instead of aiming at the highest possible acid concentration for pretreating cellulose, one should decide first which hydrolysis rate is economically viable for a process and then select accordingly the corresponding pretreatment conditions to reach the desired rate.

There are several ways to measure cellulose crystallinity index (CrI); one of the most commonly employed techniques is X-ray diffraction where the peak height is used to calculate CrI[71] (as depicted in FIG. 2). However, the major drawback of that analytical method comes from the formula itself (see corresponding experimental section), as it implies that amorphous cellulose gives a main reflection at $2\theta=18°$, which upon our analysis is definitely not the case (it is rather shifted to higher angle, ca. 19.5°). Also, the absolute values thus obtained are extremely high (>90% for Avicel), which does not seem to represent well the structure of Avicel and deviate largely from NMR analysis (60% for Avicel). In addition, the literature gives a full range of numbers for the same sample Avicel using X-ray diffraction (ranging from 62 to 87.6% using the peak height method[57-59], and from 39 to 75.3% using various others[57, 60, 73]) Under our conditions, no satisfactory resolution of the C4 carbons signals in NMR analysis could be obtained below a certain degree of crystallinity (and within reasonable acquisition time), so that X-ray diffraction was used as alternative to map the full crystallinity spectrum. Since there may be some issues with the peak intensity method to calculate degree of crystallinity from X-ray diffraction (usually values are much higher than those obtained with NMR[61] or with integrated area method, overall intensities may vary from one measurement to the other[72], plus the need to define the background baseline seems arbitrary and subject to user-based deviations; it remains a relative technique[62]), we have developed a new method to obtain consistent crystallinity index values using multivariate statistical analysis applied to X-ray diffraction spectra[74] and the values presented here were obtained from that analytical method.

FIG. 1b shows that CrI closely tracks the breakthrough behavior of reactivity (FIG. 1a) at the same amount of phosphoric acid used to pretreat the cellulose sample: the degree of crystallinity remains fairly unchanged at around 55-60% over a wide range of phosphoric acid concentrations but decreases linearly to nearly 0% within the same concentration range of 75 to 80% phosphoric acid mentioned above. Thus, the phosphoric acid effect is clearly evident: not only is it related to dissolution capacity[56], it also disrupts the crystalline structure of cellulose and can turn partially crystalline cellulose amorphous. Avicel, a microcrystalline type of cellulose, has a mixed composition (amorphous and crystalline) and our results suggest that there is a gradual transition between the two states. The more concentrated the acid solution, the more crystalline regions are turned amorphous. The capacity of cellulose samples to retain water relative to the proportion of amorphous parts has been postulated[62, 63], and was verified with the acid-treated samples. FIG. 1c shows the tight relationship between moisture content and acid concentration, supporting the conclusion on structural changes derived from crystallinity measurement, and which happen in the 75-80% acid concentration range. Upon treatment at higher acid concentrations, cellulose samples have a higher capacity to retain water, owing to the higher number of hydroxyl groups available to bind to (and adsorb) water molecules, as they are not interacting with each other anymore. A cellulose sample with 85% moisture content can theoretically accommodate 49 water molecules per glucose unit, whereas a 60% moisture content reduces this ratio down to 13 (based on the observation that 1 g Avicel yields 1.15 g of glucose at 100% conversion).

The correlation between crystallinity index and initial hydrolysis rate (FIG. 3) shows a continuous and ever-accelerating decrease in rate as crystallinity increases. The higher the degree of crystallinity, the less cellulose samples are amenable to enzymatic hydrolysis, the less reactive they are, and the less accessible. The latter is supported by the data obtained from moisture content measurement (FIG. 1c). Most aqueous reagents can only penetrate the amorphous parts of cellulose; therefore, these domains are also called the accessible regions of cellulose, and crystallinity and accessibility are closely related[62]. It seems likely that crystallinity and accessibility are related, but looking at moisture content (capacity to retain water) cannot be translated in term of enzyme accessibility, as water molecules are three orders of magnitude smaller than cellulases[64]. A highly crystalline cellulose sample has a tight structure with cellulose chains closely bound to each other, leaving too little space for enzymes to start the hydrolysis process anywhere within the cellulose crystal.

Overall, the hydrolysis rate vs. phosphoric acid concentration profile resembles a very steep and sharp sigmoid curve (FIG. 1a), so we inspected more closely the concentration range corresponding to the sigmoid region. In their review, Zhang et al. stressed that crystallinity index of cellulose was not strongly associated with hydrolysis rates[31]. Our results, on the contrary, show a very close and linear relationship between crystallinity index and initial hydrolysis rate for samples of same origin obtained after pretreatment with phosphoric acid ($R^2=0.96$, FIG. 3), showing that crystallinity is a good predictor of hydrolysis rate. More precisely, in the region between 75 and 80% phosphoric acid concentration, hydrolysis rate, crystallinity, and phosphoric acid concentration are mutually dependent parameters describing and resulting from the structural changes happening upon acid pretreatment of cellulose and related to one another by linear relationships.

We showed that phosphoric acid enables a tight control of the overall structure of cellulose in Avicel sample, which might be of importance in kinetics studies where estimation of cellulose intrinsic parameters is needed.

Cellulose Enzymatic Hydrolysis

There have been numerous controversial studies on the change of cellulose crystallinity upon enzymatic hydrolysis. Both trends (increased degree of crystallinity over conversion, no change over conversion) were observed at different levels of intensity[14, 36, 65-67]. As mentioned above, both the different types of substrate and analytical methods employed contributed to the absence of clear understanding of the mechanism of cellulases on partially crystalline cellulose. Besides, in-situ measurements of cellulose structure under reacting conditions (in aqueous buffers) are difficult as all current methods require prior isolation of cellulose and drying to some extent[29].

The crystallinity index of Avicel was monitored via X-ray diffraction during its hydrolysis by a commercial mixture of cellulases from *Trichoderma reesei* and an excess of β-glucosidase (to prevent cellobiose inhibition). The degree of crystallinity of Avicel was estimated to be 92% using the peak intensity method (which already may be subject to argument, as NMR gives an average of 60% and other X-ray diffraction results reported values between 80 and 90%, but it gives numbers for relative comparison, see above), and this index was found to fluctuate by +/−3% (data not shown). Since the absolute values are already high, a change in crystallinity might be difficult to monitor and interpret using this technique; therefore, CP/MAS $^{13}$C-NMR spectroscopy was employed as alternate method. The crystallinity index of untreated Avicel (calculated according to published method[28]) averaged 61% and was found to be constant over the course of hydrolysis, until ca. 90% conversion. No significant change could be monitored (FIG. 4). The slight fluctuations observed around this average were attributed to experimental errors.

Thus, the current thinking according to which amorphous parts of cellulose get hydrolyzed first is not consistent with these results and cannot account for the sharp decrease in rate observed along the reaction. A number of studies that reported an increasing crystallinity along enzymatic hydrolysis attributed the rate slowdown to this crystallinity change[35, 42, 66-68]. However, changes reported were often modest. Based on the results presented in this work on the relationship between crystallinity and hydrolysis rate, it does not seem physically possible that a change by some percentage points results in such dramatic drops in rate (FIG. 3 shows that a 10% increase in CrI at high CrI values leads to a 40% decrease in initial rate). Therefore, the finding that crystallinity remains constant over enzymatic hydrolysis needs to be eventually considered as definitive for pure cellulosic substrates. Other factors impeding enzymatic action, both enzyme- and substrate-related, need closer attention.

Similarly, using purified cellobiohydrolase I Cel7A from *Trichoderma reesei* (FIG. 5), instead of a mixture of cellulases, no crystallinity change was observed, however, variations in relative peak intensity in X-ray diffraction patterns showed that Cel7A attacked preferentially the (021) plane of the crystal, as the peak corresponding to this face (centered around 21°) disappeared already after 20% conversion (FIG. 6). Overall, peak intensity ratios for the other peaks were conserved (planes (101), (10 $\bar{1}$), (002) and (040) at 15, 16, 22.5 and 35°, resp.). The same trend was observed with the commercial cellulases mixture, implying no competition for this plane from the other enzymes (endoglucanases, cellobiohydrolase II and β-glucosidase) or a stronger behavior from Cel7A. The implications of this preferential attack need to be further investigated as this may provide options to engineer Cel7A and enables overall faster hydrolysis Adsorption There are multiple substrate-related factors that can influence the reaction rate in the enzymatic hydrolysis of cellulose (cf. introduction). With the results presented in this work on the determining role of crystallinity in the enzymatic activity, it is logical to wonder whether crystallinity is simply not hiding another phenomenon, specifically adsorption. Adsorption studies were therefore conducted using cellulose samples generated with various amounts of phosphoric acid and thus displaying intermediate degrees of crystallinity. Adsorption experiments were carried out at 4° C. to prevent the hydrolysis of cellulose and the resulting loss of adsorbent material that would ultimately bias the results. Also, adsorption profile at 4° C. was found to be similar to that at 50° C. after 30 min[44]. The adsorption step has been shown to be fast with half of the maximally adsorbed enzyme bound with 1-2 min and adsorption equilibrium reached after 30 min[22].

Adsorption experiments were first performed at reaction loading (amount of enzyme used to generate hydrolysis rates in FIGS. 1-3, i.e. 175 μg/mg cellulose). Surprisingly, a maximum value of adsorbed enzymes (ca. 150 μg/mg cellulose) was reached for cellulose samples with a crystallinity index below a threshold value of ca. 45% (FIG. 7a, open triangles), whereas the amount of adsorbed enzymes seemed to increase inversely and linearly with the crystallinity index at higher crystallinity values (i.e. >45%). A constant amount of adsorbed enzymes (ca. 150 μg/mg cellulose) led to faster hydrolysis reaction at lower degrees of crystallinity (i.e. <45% CrI, FIG. 7b), proving the determining role of crystallinity index in cellulose reactivity. This is most likely due to a difference in the amount of productively bound enzymes, and percentage of surface coverage. Indeed, at low degrees of crystallinity, adsorbed enzymes are being more active at same concentration (i.e. initial rates are higher, FIG. 7c), probably due to the cellulose structure being more open, and therefore preventing enzymes sitting on neighboring chains to hinder one another[69]. At very low crystallinity indexes and same adsorbed enzymes concentration, percentage of surface coverage is different because surface area is larger at lower crystallinity. Exoglucanases may also have higher chances to locate a chain end on an open structure and thus be able to start hydrolysis right away upon binding (initial rates were determined after only 2 min reaction time). Accessibility has been presented as an important factor affecting enzymatic hydrolysis rates[64]. It has been also suggested that making the substrate more amorphous increased access to the reducing-ends of cellulose, thus enhancing rates[51]. These data partially supports that hypothesis but importantly, demonstrates that the effect of improved access on hydrolysis rate is limited to higher degrees of crystallinity, while at low degrees of crystallinity, rate enhancement is strictly due to dynamic cause (independently of the adsorption phase). This can be related to recent work showing that overcrowding of enzymes on cellulose surface lowers their activity[70].

At higher enzyme loading (7 times the original loading, i.e. 1230 μg/mg cellulose), initial rates were found to be generally higher (FIG. 7c, filled circles), confirming published works[22, 39-42], but that trend was especially true at lower degrees of crystallinity. Untreated Avicel (CrI=60%) displayed indeed similar rates at both enzyme concentrations, showing that all hydrolysable fractions of cellulose were already covered by enzymes at lower loading, despite different amount of cellulases being adsorbed (high enzyme loading resulted in saturated Avicel while low enzyme loading led to more than half-saturation, binding isotherms not shown). In other words, a higher cellulose surface coverage (in an under-saturated regime) does not necessarily lead to higher rates. The role of adsorption for a given cellulose sample appears to be more crucial to the enzymatic rate at lower degrees of crystallinity (cf. grey shaded area, FIG. 7c).

At higher enzyme loading, crystallinity seems to play a minor role (FIG. 7a). Despite scattered data (due to experimental variations coming from viscous enzymatic solution and large volume added), there is a larger range of degrees of crystallinity were the amount of adsorbed enzymes linearly increases (CrI between 60 and 35%). The breakpoint can be estimated to be around 35% (compared to 45% at lower enzyme loading). Below 35% CrI, a maximum of absorbed cellulases was reached (ca. 600 μg/mg cellulose), while initial rates were still increasing (FIGS. 7a-b), highlighting also the crucial role of crystallinity in enzymatic action at higher enzyme loading. The breakpoint under which crystallinity is the only determining rate factor is expected to decrease as enzyme loading increases, as it gets comparatively harder to reach maximum binding capacity (saturation) at low degrees of crystallinity (open cellulose structure), and also maximum coverage of hydrolysable fractions (investigations underway).

Example 2

Fibrous Cellulose

Example 1 was repeated in substantially the same manner except that fibrous cellulose was substituted for Avicel and results are shown in, for example, FIG. 8b.

Example 3

Lignocellulosic Material

Example 1 may be repeated substituting a lignocellulosic material for Avicel and similar results are expected. As one skilled in the art will realize, the presence of lignin may inhibit or slow hydrolysis. Accordingly, additional data points may be beneficial when taking measurements of, for example, hydrolysis rate.

CONCLUSIONS

In summary, the direct relationship between cellulose crystallinity and enzymatic hydrolysis rate was demonstrated on pure cellulose samples (Avicel) and fibrous cellulose. FIG. 8a shows the calculated crystallinity vs. enzymatic hydrolysis rate for Avicel while FIG. 8b shows the calculated crystallinity vs. enzymatic hydrolysis rate for fibrous cellulose. In both FIGS. 8a and 8b the hydrolysis rates correspond to the amount of glucose produced in the first 2 min of the reaction with cellulases. The linear equations shown are the fits between degrees of crystallinity calculated with whole spectra and hydrolysis rates.

The use of a convenient method to reach intermediate degrees of crystallinity by varying the phosphoric acid concentration in the pretreatment step allows the exclusion of any additional parameter that might influence the enzymatic action on cellulose, such as type and source of cellulose or mixed components, and finally yields explicit proof of the tight relationship between initial cellulose crystallinity and rate of degradation by cellulases from *Trichoderma reesei*. Adsorption capacity, though influencing rate at high degrees of crystallinity and in undersaturated regime, was shown to be constant at lower degrees of crystallinity despite increasing rates, even more so at low cellulose coverage. No change on the crystallinity of cellulose over the course of the enzymatic degradation could be detected, pointing at other reasons for rates slowdown and clearly contradicting the widespread current view according to which mixed cellulose samples would get their amorphous components hydrolyzed first. As crystallinity data interpretation is not trivial, looking at initial hydrolysis rates may be an elegant alternative to determine the degree of crystallinity of pure cellulose. Constant crystallinity and decreased rates point at surface changes occurring with cellulose rapidly after the beginning of the hydrolysis. Specific features of the enzymatic mode of hydrolysis were discovered via X-ray diffraction: cellobiohydrolase I (Cel7A) preferentially attacks the (021) plane of the cellulose crystal. Despite their ability to distinguish different degrees of crystallinity, cellulases are not efficient at reducing/disrupting cellulose crystallinity, most likely due to the fact that cellulose chains are hydrolyzed as soon as their interactions with the crystal are disrupted, leaving therefore an overall unchanged crystallinity but a structure reduced in size.

Future trends for applications of cellulases in the biofuel technology should therefore focus on efficient ways to disrupt cellulose crystallinity and render the overall process economically more viable by reducing the time required to reach full conversion.

Example 4

Using Initial Hydrolysis Rate to Improve Efficiency of Enzymatic Hydrolysis

As an example, a calculation of the effort to hydrolyze fibrous cellulose (FC) from cotton linters may be reviewed. If a hydrolysis rate of 5 mg glucose/mL is measured over the first 2 minutes at pH 5 and 50° C. with a cellulose concentration of 20 g/L, the correlation of FIGS. 7, 8a, and 8b yields a degree of crystallinity of 39.4%. If 15 Units per mL of reacting solution of beta-glucosidase and 3.8 FPU (filter paper units) per mL of reacting solution of cellulases (Celluclast® from Novozymes) are used in the hydrolysis of the cellulose in question, then the initial hydrolysis rate of larger batches of the same cellulose will again be 5 mg of glucose per mL of reacting solution.

The claimed subject matter is not to be limited in scope by the specific embodiments described herein. Indeed, various modifications of the invention in addition to those described herein will become apparent to those skilled in the art from the foregoing description. Such modifications are intended to fall within the scope of the appended claims.

The citation of any publication is for its disclosure prior to the filing date and should not be construed as an admission that the present invention is not entitled to antedate such publication by virtue of prior invention and/or priority applications.

REFERENCES

1. Himmel, M. E.; Ding, S. Y.; Johnson, D. K.; Adney, W. S.; Nimlos, M. R.; Brady, J. W.; Foust, T. D., Biomass recalcitrance: Engineering plants and enzymes for biofuels production. *Science* 2007, 315, (5813), 804-807.
2. Himmel, M. E.; Ruth, M. F.; Wyman, C. E., Cellulase for commodity products from cellulosic biomass. *Current Opinion in Biotechnology* 1999, 10, (4), 358-364.
3. Wyman, C. E., What is (and is not) vital to advancing cellulosic ethanol. *Trends in Biotechnology* 2007, 25, (4), 153-157.
4. Lynd, L. R.; Laser, M. S.; Brandsby, D.; Dale, B. E.; Davison, B.; Hamilton, R.; Himmel, M.; Keller, M.; McMillan, J. D.; Sheehan, J.; Wyman, C. E., How biotech can transform biofuels. *Nature Biotechnology* 2008, 26, (2), 169-172.
5. Divne, C.; Ståhlberg, J.; Reinikainen, T.; Ruohonen, L.; Pettersson, G.; Knowles, J. K. C.; Teeri, T. T.; Jones, T. A., The 3-Dimensional Crystal-Structure of the Catalytic Core of Cellobiohydrolase-I from *Trichoderma-Reesei*. *Science* 1994, 265, (5171), 524-528.
6. Divne, C.; Ståhlberg, J.; Teeri, T. T.; Jones, T. A., High-resolution crystal structures reveal how a cellulose chain is bound in the 50 angstrom long tunnel of cellobiohydrolase I from *Trichoderma reesei*. *Journal of Molecular Biology* 1998, 275, (2), 309-325.
7. Teeri, T. T., Crystalline cellulose degradation: New insight into the function of cellobiohydrolases. *Trends in Biotechnology* 1997, 15, (5), 160-167.
8. Kipper, K.; Väljamäe, P.; Johansson, G., Processive action of cellobiohydrolase Cel7A from *Trichoderma reesei* is revealed as 'burst' kinetics on fluorescent polymeric model substrates. *Biochemical Journal* 2005, 385, 527-535.
9. Li, Y. C.; Irwin, D. C.; Wilson, D. B., Processivity, substrate binding, and mechanism of cellulose hydrolysis by *Thermobifida fusca* Ce19A. *Applied and Environmental Microbiology* 2007, 73, (10), 3165-3172.
10. Davies, G.; Henrissat, B., Structures and Mechanisms of Glycosyl Hydrolases. *Structure* 1995, 3, (9), 853-859.
11. Henrissat, B., Cellulases and Their Interaction with Cellulose. *Cellulose* 1994, 1, (3), 169-196.
12. Knowles, J.; Lehtovaara, P.; Teeri, T., Cellulase Families and Their Genes. *Trends in Biotechnology* 1987, 5, (9), 255-261.
13. Lynd, L. R.; Weimer, P. J.; van Zyl, W. H.; Pretorius, I. S., Microbial cellulose utilization: Fundamentals and biotechnology. *Microbiology and Molecular Biology Reviews* 2002, 66, (3), 506-+.
14. Zhang, Y. H. P.; Lynd, L. R., Toward an aggregated understanding of enzymatic hydrolysis of cellulose: Non-complexed cellulase systems. *Biotechnology and Bioengineering* 2004, 88, (7), 797-824.
15. Väljamäe, P.; Sild, V.; Nutt, A.; Pettersson, G.; Johansson, G., Acid hydrolosis of bacterial cellulose reveals different modes of synergistic action between cellobiohydrolase I and endoglucanase I. *European Journal of Biochemistry* 1999, 266, (2), 327-334.
16. Medve, J.; Karlsson, J.; Lee, D.; Tjerneld, F., Hydrolysis of microcrystalline cellulose by cellobiohydrolase I and endoglucanase II from *Trichoderma reesei*: Adsorption, sugar production pattern, and synergism of the enzymes. *Biotechnology and Bioengineering* 1998, 59, (5), 621-634.
17. Hoshino, E.; Shiroishi, M.; Amano, Y.; Nomura, M.; Kanda, T., Synergistic actions of exo-type cellulases in the hydrolysis of cellulose with different crystallinities. *Journal of Fermentation and Bioengineering* 1997, 84, (4), 300-306.
18. Nidetzky, B.; Hayn, M.; Macarron, R.; Steiner, W., Synergism of *Trichoderma-Reesei* Cellulases While Degrading Different Celluloses. *Biotechnology Letters* 1993, 15, (1), 71-76.
19. Henrissat, B.; Driguez, H.; Viet, C.; Schulein, M., Synergism of Cellulases from *Trichoderma-Reesei* in the Degradation of Cellulose. *Bio-Technology* 1985, 3, (8), 722-726.
20. Bansal, P.; Hall, M.; Realff, M. J.; Lee, J. H.; Bommarius, A. S., Modeling cellulase kinetics on lignocellulosic substrates. *Biotechnol Adv* 2009, 27, (6), 833-48.
21. Ståhlberg, J.; Johansson, G.; Pettersson, G., A New Model for Enzymatic-Hydrolysis of Cellulose Based on the 2-Domain Structure of Cellobiohydrolase-I. *Bio-Technology* 1991, 9, (3), 286-290.
22. Steiner, W.; Sattler, W.; Esterbauer, H., Adsorption of *Trichoderma-Reesei* Cellulase on Cellulose—Experimental-Data and Their Analysis by Different Equations. *Biotechnology and Bioengineering* 1988, 32, (7), 853-865.
23. Beldman, G.; Voragen, A. G. J.; Rombouts, F. M.; Searlevanleeuwen, M. F.; Pilnik, W., Adsorption and Kinetic-Behavior of Purified Endoglucanases and Exoglucanases from *Trichoderma-Viride*. *Biotechnology and Bioengineering* 1987, 30, (2), 251-257.
24. Bader, J.; Bellgardt, K. H.; Singh, A.; Kumar, P. K. R.; Schugerl, K., Modeling and Simulation of Cellulase Adsorption and Recycling during Enzymatic-Hydrolysis of Cellulosic Materials. *Bioprocess Engineering* 1992, 7, (5), 235-240.
25. Medve, J.; Ståhlberg, J.; Tjerneld, F., Adsorption and Synergism of Cellobiohydrolase-I and Cellobiohydrolase-Ii of *Trichoderma-Reesei* during Hydrolysis of Microcrystalline Cellulose. *Biotechnology and Bioengineering* 1994, 44, (9), 1064-1073.
26. Nidetzky, B.; Steiner, W.; Claeyssens, M., Cellulose Hydrolysis by the Cellulases from *Trichoderma-Reesei*—Adsorptions of 2 Cellobiohydrolases, 2 Endocellulases and Their Core Proteins on Filter-Paper and Their Relation to Hydrolysis. *Biochemical Journal* 1994, 303, 817-823.
27. Yang, B.; Willies, D. M.; Wyman, C. E., Changes in the enzymatic hydrolysis rate of avicel cellulose with conversion. *Biotechnology and Bioengineering* 2006, 94, (6), 1122-1128.
28. Bommarius, A. S.; Katona, A.; Cheben, S. E.; Patel, A. S.; Ragauskas, A. J.; Knudson, K.; Pu, Y., Cellulase kinetics as a function of cellulose pretreatment. *Metabolic Engineering* 2008, 10, (6), 370-381.
29. Mansfield, S. D.; Mooney, C.; Saddler, J. N., Substrate and enzyme characteristics that limit cellulose hydrolysis. *Biotechnology Progress* 1999, 15, (5), 804-816.
30. Xu, F.; Ding, H. S., A new kinetic model for heterogeneous (or spatially confined) enzymatic catalysis: Contributions from the fractal and jamming (overcrowding) effects. *Applied Catalysis a-General* 2007, 317, (1), 70-81.
31. Zhang, Y. H. P.; Himmel, M. E.; Mielenz, J. R., Outlook for cellulase improvement: Screening and selection strategies. *Biotechnology Advances* 2006, 24, (5), 452-481.
32. McLean, B. W.; Boraston, A. B.; Brouwer, D.; Sanaie, N.; Fyfe, C. A.; Warren, R. A. J.; Kilburn, D. G.; Haynes, C. A., Carbohydrate-binding modules recognize fine substructures of cellulose. *Journal of Biological Chemistry* 2002, 277, (52), 50245-50254.
33. Puri, V. P., Effect of Crystallinity and Degree of Polymerization of Cellulose on Enzymatic Saccharification. *Biotechnology and Bioengineering* 1984, 26, (10), 1219-1222.
34. Fan, L. T.; Lee, Y. H., Kinetic-Studies of Enzymatic-Hydrolysis of Insoluble Cellulose—Derivation of a Mechanistic Kinetic-Model. *Biotechnology and Bioengineering* 1983, 25, (11), 2707-2733.
35. Ohmine, K.; Ooshima, H.; Harano, Y., Kinetic-Study on Enzymatic-Hydrolysis of Cellulose by Cellulase from *Trichoderma-Viride*. *Biotechnology and Bioengineering* 1983, 25, (8), 2041-2053.
36. Fan, L. T.; Lee, Y. H.; Beardmore, D. H., Mechanism of the Enzymatic-Hydrolysis of Cellulose—Effects of Major Structural Features of Cellulose on Enzymatic-Hydrolysis. *Biotechnology and Bioengineering* 1980, 22, (1), 177-199.
37. Zhu, L.; O'Dwyer, J. P.; Chang, V. S.; Granda, C. B.; Holtzapple, M. T., Structural features affecting biomass enzymatic digestibility. *Bioresource Technology* 2008, 99, (9), 3817-3828.
38. Berlin, A.; Gilkes, N.; Kurabi, A.; Bura, R.; Tu, M. B.; Kilburn, D.; Saddler, J., Weak lignin-rinding enzymes—A novel approach to improve activity of cellulases for hydrolysis of lignocellulosics. *Applied Biochemistry and Biotechnology* 2005, 121, 163-170.
39. Sattler, W.; Esterbauer, H.; Glatter, O.; Steiner, W., The Effect of Enzyme Concentration on the Rate of the Hydrolysis of Cellulose. *Biotechnology and Bioengineering* 1989, 33, (10), 1221-1234.

40. Lee, Y. H.; Fan, L. T., Kinetic-Studies of Enzymatic-Hydrolysis of Insoluble Cellulose—Analysis of the Initial Rates. *Biotechnology and Bioengineering* 1982, 24, (11), 2383-2406.

41. Ryu, D. D. Y.; Lee, S. B., Enzymatic-Hydrolysis of Cellulose—Determination of Kinetic-Parameters. *Chemical Engineering Communications* 1986, 45, (1-6), 119-134.

42. Medve, J.; Stahlberg, J.; Tjerneld, F., Adsorption and Synergism of Cellobiohydrolase-I and Cellobiohydrolase-Ii of *Trichoderma-Reesei* during Hydrolysis of Microcrystalline Cellulose. *Biotechnology and Bioengineering* 1994, 44, (9), 1064-1073.

43. Klyosov, A. A.; Mitkevich, O. V.; Sinitsyn, A. P., Role of the Activity and Adsorption of Cellulases in the Efficiency of the Enzymatic-Hydrolysis of Amorphous and Crystalline Cellulose. *Biochemistry* 1986, 25, (3), 540-542.

44. Lee, S. B.; Shin, H. S.; Ryu, D. D. Y.; Mandels, M., Adsorption of Cellulase on Cellulose—Effect of Physicochemical Properties of Cellulose on Adsorption and Rate of Hydrolysis. *Biotechnology and Bioengineering* 1982, 24, (10), 2137-2153.

45. Schulein, M., Enzymatic properties of cellulases from *Humicola insolens*. *Journal of Biotechnology* 1997, 57, (1-3), 71-81.

46. Wood, T. M., Cellulase of *Fusarium-Solani*. *Biochemical Journal* 1971, 121, (3), 353-&.

47. Andersen, N.; Johansen, K. S.; Michelsen, M.; Stenby, E. H.; Krogh, K. B. R. M.; Olsson, L., Hydrolysis of cellulose using mono-component enzymes shows synergy during hydrolysis of phosphoric acid swollen cellulose (PASC), but competition on Avicel. *Enzyme and Microbial Technology* 2008, 42, (4), 362-370.

48. Szijarto, N.; Siika-aho, M.; Tenkanen, M.; Alapuranen, M.; Vehmaanpera, J.; Reczeya, K.; Viikari, L., Hydrolysis of amorphous and crystalline cellulose by heterologously produced cellulases of *Melanocarpus albomyces*. *Journal of Biotechnology* 2008, 136, (3-4), 140-147.

49. Stone, J. E.; Scallan, A. M.; Donefer, E.; Ahlgren, E., Digestibility as a Simple Function of a Molecule of Similar Size to a Cellulase Enzyme. *Advances in Chemistry Series* 1969, (95), 219-&.

50. Zhang, Y. H. P.; Cui, J. B.; Lynd, L. R.; Kuang, L. R., A transition from cellulose swelling to cellulose dissolution by o-phosphoric acid: Evidence from enzymatic hydrolysis and supramolecular structure. *Biomacromolecules* 2006, 7, (2), 644-648.

51. Jeoh, T.; Ishizawa, C. I.; Davis, M. F.; Himmel, M. E.; Adney, W. S.; Johnson, D. K., Cellulase digestibility of pretreated biomass is limited by cellulose accessibility. *Biotechnology and Bioengineering* 2007, 98, (1), 112-122.

52. Zhang, Y. H. P.; Lynd, L. R., Determination of the number-average degree of polymerization of cellodextrins and cellulose with application to enzymatic hydrolysis. *Biomacromolecules* 2005, 6, (3), 1510-1515.

53. Weimer, P. J.; Lopezguisa, J. M.; French, A. D., Effect of Cellulose Fine-Structure on Kinetics of Its Digestion by Mixed Ruminal Microorganisms Invitro. *Applied and Environmental Microbiology* 1990, 56, (8), 2421-2429.

54. Israilides, C. J.; Grant, G. A.; Han, Y. W., Sugar Level, Fermentability, and Acceptability of Straw Treated with Different Acids. *Applied and Environmental Microbiology* 1978, 36, (1), 43-46.

55. Um, B. H.; Karim, M. N.; Henk, L. L., Effect of sulfuric and phosphoric acid pretreatments on enzymatic hydrolysis of corn stover. *Applied Biochemistry and Biotechnology* 2003, 105, 115-125.

56. Moxley, G.; Zhu, Z. G.; Zhang, Y. H. P., Efficient sugar release by the cellulose solvent-based lignocellulose fractionation technology and enzymatic cellulose hydrolysis. *Journal of Agricultural and Food Chemistry* 2008, 56, (17), 7885-7890.

57. Thygesen, A.; Oddershede, J.; Lilholt, H.; Thomsen, A. B.; Stahl, K., On the determination of crystallinity and cellulose content in plant fibres. *Cellulose* 2005, 12, (6), 563-576.

58. De Souza, I. J.; Bouchard, J.; Methot, M.; Berry, R.; Argyropoulos, D. S., Carbohydrates in oxygen delignification. Part I: Changes in cellulose crystallinity. *Journal of Pulp and Paper Science* 2002, 28, (5), 167-170.

59. Gama, F. M.; Teixeira, J. A.; Mota, M., Cellulose Morphology and Enzymatic Reactivity—a Modified Solute Exclusion Technique. *Biotechnology and Bioengineering* 1994, 43, (5), 381-387.

60. Ardizzone, S.; Dioguardi, F. S.; Mussini, T.; Mussini, P. R.; Rondinini, S.; Vercelli, B.; Vertova, A., Microcrystalline cellulose powders: structure, surface features and water sorption capability. *Cellulose* 1999, 6, (1), 57-69.

61. Park, S.; Johnson, D. K.; Ishizawa, C. I.; Parilla, P. A.; Davis, M. F., Measuring the crystallinity index of cellulose by solid state C-13 nuclear magnetic resonance. *Cellulose* 2009, 16, (4), 641-647.

62. Bertran, M. S.; Dale, B. E., Determination of Cellulose Accessibility by Differential Scanning calorimetry. *Journal of Applied Polymer Science* 1986, 32, (3), 4241-4253.

63. Kimura, M.; Hatakeya. T; Nakano, J., Dsc Study on Recrystallization of Amorphous Cellulose with Water. *Journal of Applied Polymer Science* 1974, 18, (10), 3069-3076.

64. Hong, J.; Ye, X. H.; Zhang, Y. H. P., Quantitative determination of cellulose accessibility to cellulase based on adsorption of a nonhydrolytic fusion protein containing CBM and GFP with its applications. *Langmuir* 2007, 23, (25), 12535-12540.

65. Ramos, L. P.; Zandona, A.; Deschamps, F. C.; Saddler, J. N., The effect of *Trichoderma* cellulases on the fine structure of a bleached softwood kraft pulp. *Enzyme and Microbial Technology* 1999, 24, (7), 371-380.

66. Chen, Y.; Stipanovic, A. J.; Winter, W. T.; Wilson, D. B.; Kim, Y. J., Effect of digestion by pure cellulases on crystallinity and average chain length for bacterial and microcrystalline celluloses. *Cellulose* 2007, 14, (4), 283-293.

67. Lee, S. B.; Kim, I. H.; Ryu, D. D. Y.; Taguchi, H., Structural-Properties of Cellulose and Cellulase Reaction-Mechanism. *Biotechnology and Bioengineering* 1983, 25, (1), 33-51.

68. Ooshima, H.; Sakata, M.; Harano, Y., Adsorption of Cellulase from *Trichoderma-Viride* on Cellulose. *Biotechnology and Bioengineering* 1983, 25, (12), 3103-3114.

69. Väljamäe, P.; Sild, V.; Pettersson, G.; Johansson, G., The initial kinetics of hydrolysis by cellobiohydrolases I and II is consistent with a cellulose surface-erosion model. *European Journal of Biochemistry* 1998, 253, (2), 469-475.

70. Igarashi, K.; Wada, M.; Hori, R.; Samejima, M., Surface density of cellobiohydrolase on crystalline celluloses—A critical parameter to evaluate enzymatic kinetics at a solid-liquid interface. *Febs Journal* 2006, 273, (13), 2869-2878.

71. Segal, L.; Creely, J. J.; Martin, A. E.; Conrad, C. M., An empirical method for estimating the degree of crystallinity of native cellulose using the x-ray diffractometer. *Textile Research Journal* 1959, 29, 786-794.
72. Krässig, H. A., Cellulose: Structure, accessibility and reactivity. 1993, 11, Polymer Monographs, Gordon and Breach Science publisher, New York
73. Soltys, J.; Lisowski, Z.; Knapczyk, J., X-Ray Diffraction Study of the Crystallinity Index and the Structure of the Microcrystalline Cellulose. *Acta Pharmaceutica Technologica* 1984, 30, 174-180.
74. Bansal, P.; Hall, M.; Realff, M. J.; Lee, J. H.; Bommarius, A. B., Multivariate statistical analysis of X-ray data from cellulose: A new method to determine degree of crystallinity and predict hydrolysis rates. 101 *Bioresource Technol.* 4461-4471 (2010).
75. Hall et al., "Cellulose Crystallinity—a key predictor of the enzymatic hydrolysis rate", FEBS Journal 277 (2010) 1571-1582.

What is claimed is:

1. A method for producing glucose for fermentation said method comprising:
   (a) measuring the initial hydrolysis rate of a biomass;
   (b) correlating the measured initial hydrolysis rate with a crystallinity index of standard cellulosic materials to project a crystallinity indicative of overall enzymatic hydrolysis susceptibility wherein the crystallinity index was determined by applying multivariate statistical analysis to X-ray diffraction spectra, solid state cross-polarization/magic angle spinning nuclear magnetic resonance spectra, infrared spectra, differential scanning calorimetry heat capacity temperature plots, or a combination thereof;
   (c) selecting one or more of the reaction conditions of steps (d)-(f) based on the projected crystallinity of the biomass;
   (d) treating a biomass with acid and heat to produce a composition mixture comprising cellulose suitable for enzymatic hydrolysis;
   (e) enzymatically hydrolyzing at least a portion of the cellulose of step (d) to form a composition comprising glucose; and
   (f) utilizing glucose in an aerobic or anaerobic fermentation process.

2. The method of claim 1 wherein the glucose is fermented to a product selected from the group consisting of alcohols, fatty alcohols, hydrocarbons, fatty acids, tryglycerides, terpenes, and combinations thereof.

3. The method of claim 1 wherein said one or more appropriate conditions are selected from the group consisting of type of enzyme, amount of enzyme, reaction time, and reaction temperature.

4. The method of claim 1 wherein the initial hydrolysis rate is measured by x-ray diffraction, solid state cross-polarization/magic angle spinning nuclear magnetic resonance, infrared spectroscopy, differential scanning calorimetry, or a combination thereof.

5. The method of claim 1 wherein the initial hydrolysis rate is measured by x-ray diffraction and wherein the crystallinity index was determined by applying multivariate statistical analysis to X-ray diffraction spectra.

6. The method of claim 1 the biomass is selected from the group consisting of a wood or forestry residue, municipal paper waste, algae, agricultural residue, and a dedicated energy crop.

* * * * *